United States Patent
Coates et al.

(10) Patent No.: US 8,147,898 B2
(45) Date of Patent: Apr. 3, 2012

(54) LOW TEMPERATURE DRUG DEPOSITION

(75) Inventors: Paul Coates, Corte Madera, CA (US); Brian Cook, Windsor, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 918 days.

(21) Appl. No.: 12/179,783

(22) Filed: Jul. 25, 2008

(65) Prior Publication Data

US 2010/0021620 A1   Jan. 28, 2010

(51) Int. Cl.
- *A61L 33/00* (2006.01)
- *B05D 3/00* (2006.01)
- *A61K 9/14* (2006.01)
- *A61F 2/06* (2006.01)

(52) U.S. Cl. ...... 427/2.24; 427/2.25; 424/423; 424/487; 623/1.11; 623/1.42; 623/1.46

(58) Field of Classification Search ............... 427/2.24, 427/2.25; 424/423, 487; 623/1.11, 1.42, 623/1.46

See application file for complete search history.

(56) References Cited

U.S. PATENT DOCUMENTS

| | | |
|---|---|---|
| 4,733,665 A | 3/1988 | Palmaz |
| 4,800,882 A | 1/1989 | Gianturco |
| 4,886,062 A | 12/1989 | Wiktor |
| 5,133,732 A | 7/1992 | Wiktor |
| 5,292,331 A | 3/1994 | Boneau |
| 5,421,955 A | 6/1995 | Lau et al. |
| 5,935,162 A | 8/1999 | Dang |
| 6,090,127 A | 7/2000 | Globerman |
| 6,730,116 B1 | 5/2004 | Wolinsky et al. |
| 2002/0038767 A1 | 4/2002 | Trozera |
| 2004/0215313 A1* | 10/2004 | Cheng ............ 623/1.11 |
| 2005/0074545 A1 | 4/2005 | Thomas |
| 2005/0220840 A1* | 10/2005 | DeWitt et al. ........ 424/423 |
| 2005/0273161 A1 | 12/2005 | Malik et al. |

FOREIGN PATENT DOCUMENTS

WO   WO99/16386   4/1999

* cited by examiner

*Primary Examiner* — Timothy J. Kugel
*Assistant Examiner* — Atnaf Admasu

(57) ABSTRACT

A drug coating is formed by vaporizing a drug in a deposition chamber having an implantable medical device such as a stent loaded therein. A vacuum is utilized to lower the pressure within the deposition chamber, thereby reducing the temperature necessary to vaporize the drug. The drug is then deposited onto the implantable medical device while in a vapor phase to form the drug coating.

20 Claims, 5 Drawing Sheets

LOW TEMPERATURE DRUG DEPOSITION

FIELD OF THE INVENTION

This invention relates generally to a drug coating and methods for forming a drug coating on an implantable medical device.

BACKGROUND OF THE INVENTION

Endovascular stents are coated frequently with a polymer that contains one or more therapeutic substances within a polymeric matrix to improve the efficacy of the stents. These substances are eluted from the stent coating to the tissue bed surrounding the implanted stent. The effectiveness of these therapeutic substances is generally improved because localized levels of medication may be higher and potentially more successful than orally or intravenously delivered drugs, which are distributed throughout the body rather than concentrated at the location of most need. Drugs released from tailored stent coatings may have controlled, time-release qualities, eluting their bioactive agents over hours, weeks or even months.

Various methods of coating a stent or other implantable medical device with one or more polymers containing one or more therapeutic substances are known. For example, a common solvent or a pair of solvents may be used to dissolve drugs and polymers, including copolymers, terpolymers or polymer blends. The resulting drug-polymer solution is then applied on the stent by spraying, dipping, brushing, or rolling. The stent is then dried, for instance in a vacuum or oven, to evaporate the solvent, leaving the therapeutic substance or therapeutic substance and polymer coating on the stent. Problems may arise in getting polymer coatings to adhere to stents, particularly stents made of cobalt-based alloys. Most coronary stents are finished by electrochemical polishing for surface smoothness. A smooth surface is desirable because early research has shown that a stent with a rough surface results in more platelet cell adhesion, thrombus, inflammation, and restenosis than a smoothly polished stent. The smooth surface may pose a challenge to the coating, however. Due to the very different nature of the polymer and the metallic substrate, a polymeric coating does not easily adhere to the metallic substrate. If the coating does not adhere well to the metal surface, it may cause problems such as coating delamination, irregular drug release profiles, or embolism caused by broken and detached debris from the coating.

It is also known in the art to coat a stent with a polymer that does not contain a therapeutic substance, for example, to form a sealant overcoat layer or primer coating. Methods of applying a polymer coating include vapor phase deposition. Vapor phase deposition typically entails vaporizing a dimer, and applying energy to the vaporized dimer to create an active monomer. The system set up is such that the monomer is deposited onto the stent and polymerizes in-situ, thereby creating a polymer coating around the stent. However, vapor deposition is not used for applying a therapeutic substance coating because the high temperatures associated with the process may cause the drugs to break down and lose their efficacy.

The present invention is related to an improved drug coating for an implantable medical device.

BRIEF SUMMARY OF THE INVENTION

Embodiments of the present invention relate to a method of coating an implantable medical device. An implantable medical device is provided within a deposition chamber. A drug is introduced into the deposition chamber and vaporized such that at least a portion of the vaporized drug forms a drug coating on the implantable medical device. A vacuum is utilized to lower the pressure within the deposition chamber, thereby reducing the temperature necessary to vaporize the drug.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, where like reference numbers indicate identical or functionally similar elements. Embodiments in accordance with the present invention are directed to methods for coating the surface of an implantable medical device, such as a stent or graft, which are often referred to as endoprostheses. In the discussion below, the example of a stent is provided. Practitioners will appreciate, however, that the methods and structures of the present invention are not limited to a stent, but rather extend to all implantable devices having a surface upon which a coating can be deposited, such as artificial joints, bones, pacemakers, and the like.

Figure 1:
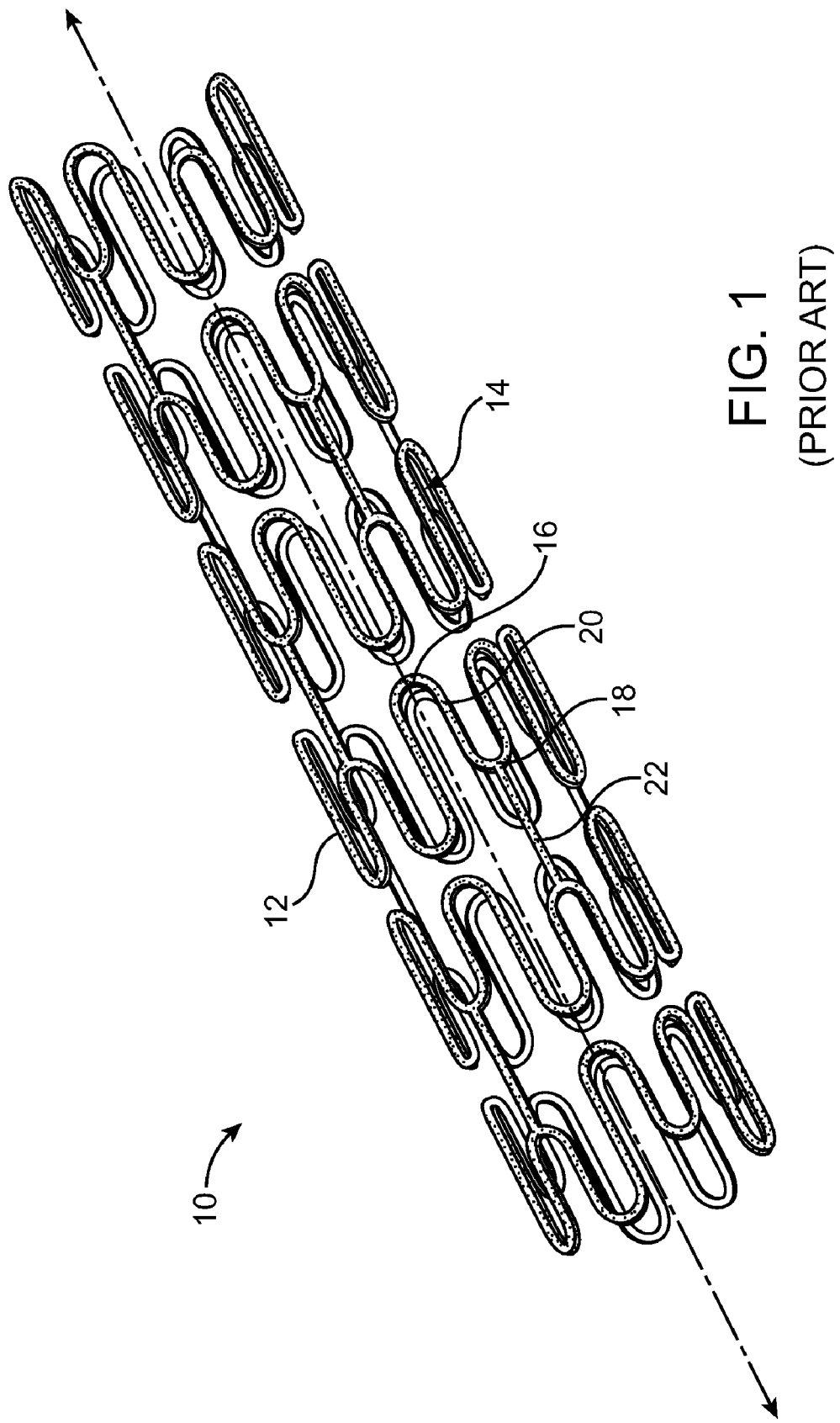
FIG. 1 is a schematic view of an exemplary stent that may be coated by a method in accordance with embodiments of the present invention.

FIG. 1 illustrates an exemplary stent 10 in accordance with an embodiment of the present invention. Stent 10 is a patterned tubular device that includes a plurality of radially expandable cylindrical rings 12. Cylindrical rings 12 are formed from struts 14 formed in a generally sinusoidal pattern including peaks 16, valleys 18, and generally straight segments 20 connecting peaks 16 and valleys 18. Connecting links 22 connect adjacent cylindrical rings 12 together. In FIG. 1, connecting links 22 are shown as generally straight links connecting a peak 16 of one ring 12 to a valley 18 of an adjacent ring 12. However, connecting links 22 may connect a peak 16 of one ring 12 to a peak 16 of an adjacent ring, or a valley to a valley, or a straight segment to a straight segment. Further, connecting links 22 may be curved. Connecting links 22 may also be excluded, with a peak 16 of one ring 12 being directly attached to a valley 18 of an adjacent ring 12, such as by welding, soldering, or the manner in which stent 10 is formed, such as by etching the pattern from a flat sheet or a tube. It will be appreciated by those skilled in the art that stent 10 of FIG. 1 is merely an exemplary stent and that stents of various forms and methods of fabrication can be used. For example, in a typical method of making a stent, a thin-walled, small diameter metallic tube is cut to produce the desired stent pattern, using methods such as laser cutting or chemical etching. The cut stent may then be descaled, polished, cleaned and rinsed. Some examples of methods of forming stents and structures for stents which are suitable for use in embodiments hereof are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,724 to Wiktor, U.S. Pat. No. 5,292,331 to Boneau, U.S. Pat. No. 5,421,955 to Lau, U.S. Pat. No. 5,935,162 to Dang, U.S. Pat. No. 6,090,127 to Globerman, and U.S. Pat. No. 6,730,116 to Wolinsky et al., each of which is incorporated by reference in its entirety herein.

Typical materials used for stent 10 are metals or alloys, examples of which include, but are not limited to, stainless steel, "MP35N," "L605" nickel titanium alloys such as Nitinol (e.g., ELASTINITE® by Advanced Cardiovascular Systems, Inc., Santa Clara, Calif.), tantalum, platinum-iridium alloy, gold, magnesium, or combinations thereof. "MP35N" and "L605" are trade names for alloys of cobalt chromium and nickel. MP35N is available from standard Press Steel Co., Jenkintown, Pa. "MP35N" consists of 35% cobalt, 35% nickel, 20% chromium, and 10% molybdenum.

Figure 2:
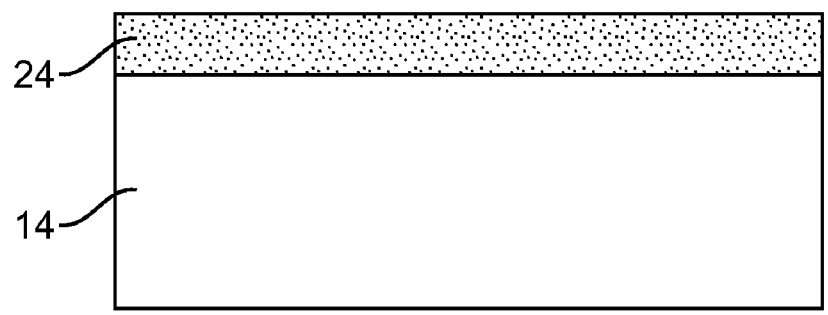
FIG. 2 is a cross-sectional view of a stent strut of FIG. 1 in accordance with an embodiment hereof.

Referring now to FIG. 2, a therapeutic substance or drug coating 24 covers stent 10. Drug coating 24 is formed by vaporizing a drug in a deposition chamber having stent 10 loaded therein. A vacuum is utilized to lower the pressure within the deposition chamber, thereby reducing the temperature necessary to vaporize the drug. The temperature necessary to vaporize the drug must be below the temperature at which the drug is unstable, so that the drug maybe vaporized without breaking down and losing efficacy. In one embodiment, the pressure within the deposition chamber is lowered to approximately $10^{-5}$ atm. In another embodiment, the pressure within the deposition chamber may be in the range of $10^{-3}$ to $10^{-7}$ atm. Such a lower pressure reduces the temperature required for vaporizing the drug, thus preserving the efficacy of the drug and allowing it to be deposited onto stent 10 in a vapor phase.

Drug vapor deposition allows for a uniform and consistent coating to be formed on stent 10. In addition, drug vapor deposition allows for improved control over the thickness and weight of the coating, and allows for multiple implantable medical devices to be coated in one batch in a predictable and repeatable manner. Further, drug vapor deposition does not require the use of a solvent, which is beneficial to the environment and may eliminate regulatory burdens, processing steps such as drying and inspection steps during the manufacturing process.

Figure 3:
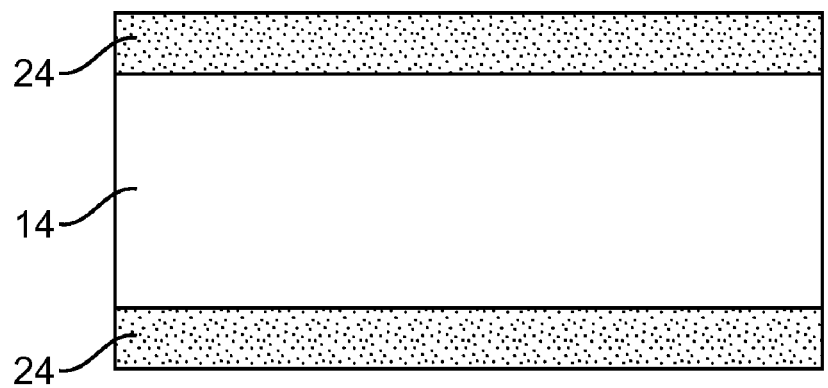
FIG. 3 is a cross-sectional view of a stent strut of FIG. 1 in accordance with another embodiment hereof.
Figure 4:
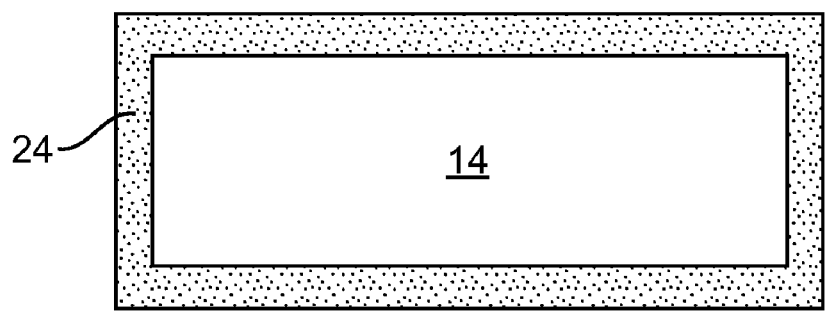
FIG. 4 is a cross-sectional view of a stent strut of FIG. 1 in accordance with another embodiment hereof.

FIGS. 2-4 are exemplary cross-sectional views that illustrate various embodiments of the present invention wherein drug coating 24 may cover one or more surfaces of stent 10, including an inner surface, an outer surface, and/or side surfaces of the stent struts. It will be appreciated by those skilled in the art that the rectangular cross-sections of FIGS. 2-4 are merely exemplary and that stents of various cross-sections such as circular or ellipsoidal can be used. More particularly, FIG. 2 is a cross-sectional view of stent strut 14 of FIG. 1 with a vaporized drug coating 24 on an outer surface of the strut that is deployed against the vessel wall. In order to selectively coat only the outer surface of the stent, a masking or other suitable technique may be utilized to maintain the remaining surfaces, i.e., the side surfaces and the inner surface, coating-free. For example, the stent may be mounted onto a rod or mandrel having an outer diameter that essentially is the same as the inner diameter of the stent. Accordingly, vaporized drug coating 24 would be prevented from being deposited onto the inner surface of the stent. FIG. 3 is a cross-sectional view of stent strut 14 with a vaporized drug coating 24 on outer and inner surfaces of the strut. As in the above embodiment, in order to selectively coat only the outer and inner surfaces of the stent, a masking or other suitable technique may be utilized to maintain the remaining surfaces, i.e., the side surfaces, coating-free. FIG. 4 is a cross-sectional view of stent strut 14 with a vaporized drug coating 24 on outer, inner and side surfaces of the strut. In one embodiment, stent 10 may be charged with an electrostatic charge so as to attract the vaporized drug and increase the amount of the vaporized drug coated onto the stent.

The drug must be capable of being vaporized and deposited without changing structure and losing efficacy, and in one embodiment, is a low molecular weight drug. Lower molecular weight materials tend to evaporate at lower temperatures. In order to vaporize the drug, the drug is heated to a predetermined temperature that causes the drug to change from its solid phase into a vaporous state. As previously mentioned, vapor deposition has not been used heretofore for applying a therapeutic substance coating because the high temperatures customarily associated with the process may cause the drugs to break down and lose their efficacy. However, in the present invention, a vacuum is utilized to lower the pressure in the deposition chamber where the drug is vaporized. The lower pressure reduces the temperature necessary to vaporize the drug, thus preserving the efficacy of the drug and allowing it to be deposited in a vapor phase.

Therapeutic substances that may be vaporized to form drug coating 24 include, but are not limited to, antineoplastic, antimitotic, antiinflammatory, antiplatelet, anticoagulant, anti-fibrin, antithrombin, antiproliferative, antibiotic, antioxidant, and antiallergic substances as well as combinations thereof. Anti-proliferative agents may include drugs such as amlodipine, doxazosin, sirolimus, everolimus, zotarolimus, and other—limus family compounds. Examples of antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, and thrombin inhibitors such as Angiomax™ (Biogen, Inc., Cambridge, Mass.). While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

Stent 10 is not limited to a single layer of drug coating 24. In one embodiment, stent 10 may include two or more drug coatings or layers. Drug vapor deposition is particularly beneficial for creating two or more distinct coatings. More particularly, when a conventional drug-solvent solution is applied to a stent in two or more separate coatings, the coatings tend to intermix or overlap to some extent due to the composition of the drug-solvent solution. However, drug vapor deposition results in a drug coating that does not intermix with an underlying coating or layer. The therapeutic substance of a first drug coating can be, but need not necessarily be, different from the therapeutic substance of a second drug coating. The use of different materials in the drug layers allows the stent to perform more than a single therapeutic function. As such multiple drug coating layers can be used to achieve different therapeutic substance release profiles. For example, if it is desired to release two therapeutic substances sequentially, two drug coating layers may be used. A therapeutic substance in an outer drug coating layer will be released first, and a therapeutic substance in an inner drug coating layer will be released after the outer drug coating layer has wholly or partially dissolved.

Figure 5:
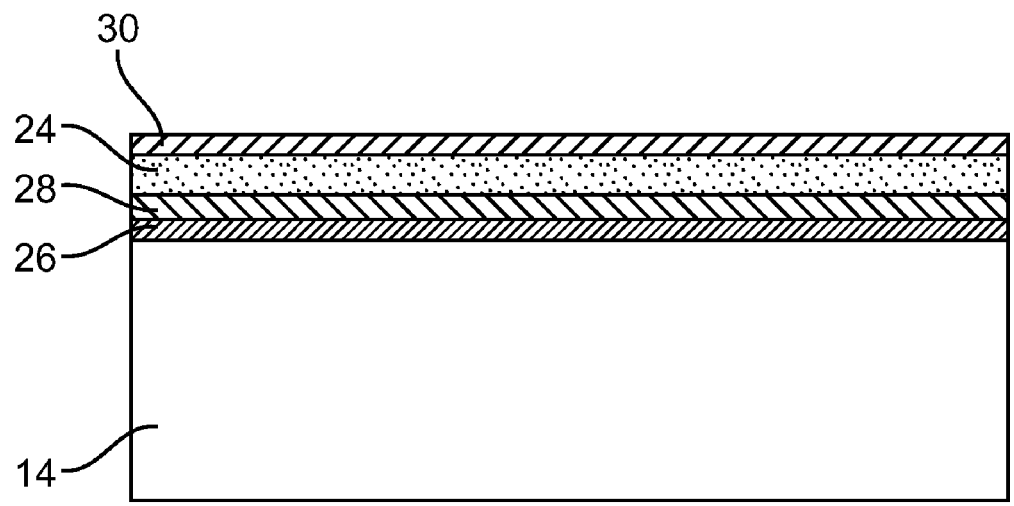
FIG. 5 is a cross-sectional view of a stent strut of FIG. 1 in accordance with another embodiment hereof.

FIG. 5 illustrates another embodiment of the present invention. As shown in FIG. 5, in addition to drug coating 24, stent 10 may include several layers or coatings. Stent 10 may include a precursor base coating 26 applied directly to stent 10. In one embodiment, base coating 26 may be silane. Base coating 26 is applied externally, outside of the deposition chamber, in a dipping, rolling, spraying, or brushing process. Base coating 26 is permitted to dry, and then stent 10 may be loaded into the deposition chamber. Although FIG. 5 illustrates the several layers or coatings on only an outer surface of the stent, such layers may cover one or more surfaces of stent 10, including an inner surface, an outer surface, and/or side surfaces of the stent struts, as described above.

Figure 6:
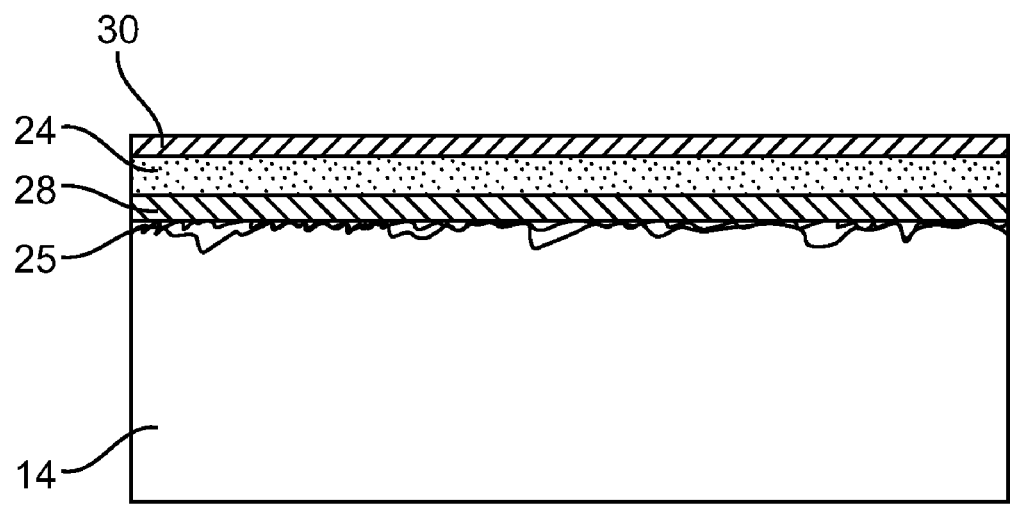
FIG. 6 is a cross-sectional view a stent strut of FIG. 1 in accordance with another embodiment hereof.

In an alternate embodiment illustrated in FIG. 6, stent 10 may include a roughened outer stent surface 25 as an alternative to base coating 26. The roughened outer stent surface may be formed by any suitable method known in the art, such as by an abrasion process, a sputtering or sintering process, a chemical etching process, or an ion beam etching process, that creates pits or irregularities on the surface(s) of stent 10. In sputtering, an energy beam, for instance an ion beam, is directed at a target formed of the material which is to be deposited on the substrate. In ion beam etching, an ion beam is irradiated onto a specimen target in a high vacuum and physically sputters away the irradiated surface atoms. Although FIG. 6 illustrates the several layers or coatings on only an outer surface of the stent, such coatings may cover one or more surfaces of stent 10, including an inner surface, an outer surface, and/or side surfaces of the stent struts, as described above.

Referring to FIGS. 5 and 6, stent 10 may also include a primer coating or tie layer 28 to improve adherence of drug coating 24 to stent 10. Primer coating 28 improves the adhesion of drug coating 24, thus increasing the amount of drug that can be deposited and allowing the drug to be deposited in a more uniform layer. Primer coating 28 is a medical grade primer that does not contain a therapeutic substance and may be applied by any suitable method known in the art. For example, primer coating 28 may be applied by dipping, rolling, spraying, brushing, or vapor deposition. In one embodiment, primer coating 28 is applied via vapor phase polymerization. Preferably, the layer automatically polymerizes upon condensation from the vapor phase, without the action of any solvent, catalysts or similar polymerization promoters or any curative agent or activity such as heating, the application of visible or ultraviolet light, radiation, ultrasound, or the like. Stent 10 may be loaded within the deposition chamber, and primer coating 28 is applied prior to application of drug coating 24. Primer coating 28 is a polymer coating applied around the stent by vaporizing a dimer, and applying energy to the vaporized dimer such that the polymer is deposited onto the stent. After primer coating 28 is applied, the stent does not have to be removed from the deposition chamber. Rather, one or more quality check(s) may be performed to ensure that primer coating 28 has been properly applied to the stent and upon such approval, drug coating 24 may then be applied. For example, the operator may run a quality check to ensure that primer coating 28 is applied in a consistent manner, i.e., the thickness of the coating is uniform and consistent over separate batches or runs. Once a consistent coating thickness is established and confirmed, such consistency may then be inferred for all runs so that drug coating 24 may be applied without an intermediate evaluation. Periodic confirmation or testing may be performed to confirm the consistency of the thickness of the primer coating.

Stent 10 may further include a top layer or overcoat 30 applied over drug coating 24. In one embodiment, overcoat 30 is deposited over drug coating 24 to provide a controlled release of the drug when stent 10 is positioned in the vascular system of a patient. Thus, drug coating 24 lies under overcoat 30 rather than being dispersed within or throughout it. Overcoat 30 also protects drug coating 24 during deployment of stent 10, for example, during insertion of stent 10 through a catheter and into the vascular system or elsewhere in the patient. Overcoat 30 may be applied by any suitable method known in the art, such as by dipping, rolling, spraying, brushing, or sputtering. In one embodiment, overcoat 30 may include a polymer deposited on drug coating 24 by vapor phase polymerization as described above with respect to primer coating 28. As previously mentioned, drug vapor deposition is particularly beneficial for creating two or more distinct coatings that do not intermix or overlap. If applied by vapor phase polymerization, the stent does not have to be removed from the deposition chamber after drug coating 24 is applied. Overcoat 30 may be applied after a quality check is performed to ensure that drug coating 24 has been properly applied to the stent.

In one embodiment, overcoat 30 is deposited to include pores to allow for control over the release rate of material from drug coating 24. The thickness, porosity and the like of overcoat 30 may be carefully selected so as to provide such control. In another embodiment, overcoat 30 is a biodegradable polymer that dissolves or breaks down within a vessel such that drug coating 24 is released or emitted into a body lumen for treatment thereof. A bioabsorbable polymer biodegrades or breaks down in the body and is not present sufficiently long after implantation to cause an adverse local response. Bioabsorbable polymers are gradually absorbed or eliminated by the body by hydrolysis, metabolic process, bulk, or surface erosion. Examples of bioabsorbable, biodegradable materials include but are not limited to chitosan, caprolactone, modified cellulose, collagen, albumin, casein, polysaccharides (PSAC), polylactide (PLA), polylactide [poly-L-lactide (PLLA), poly-D-lactide (PDLA)], polyglycol (PGA), poly-D,L-lactide-co-glycolide (PDLLA/PGA), polyhydroxybutyric acid (PHB), polyhydroxyvaleric acid (PHV), polyalkylcarbonate, polyorthoester, polymalic acid (PMLA), polyanhydrides, polyphosphazenes, polyamino acids or related copolymers materials. Each type of biodegradable polymer has a characteristic degradation rate in the body. The dissolution rate of overcoat 30 may be tailored by controlling the type of biodegradable polymer, the thickness and/or density of the biodegradable polymer, and/or the nature of the biodegradable polymer. In addition, characteristics such as the chemical composition and molecular weight of the biodegradable polymer may also be selected in order to control the dissolution rate of overcoat 30.

Figure 7:
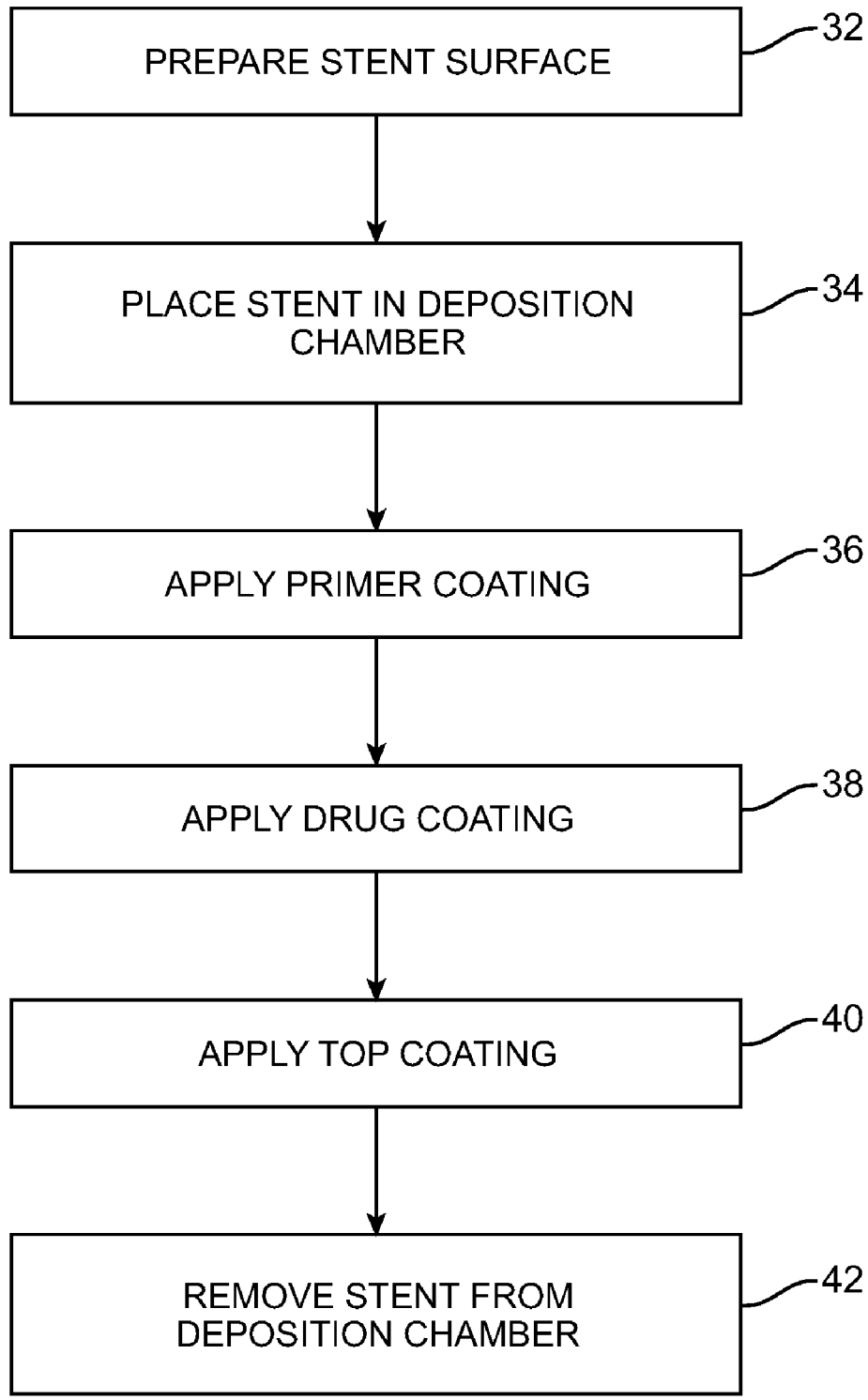
FIG. 7 is a flow chart of the method steps for coating a stent according to an embodiment of the present invention.
Figure 8:
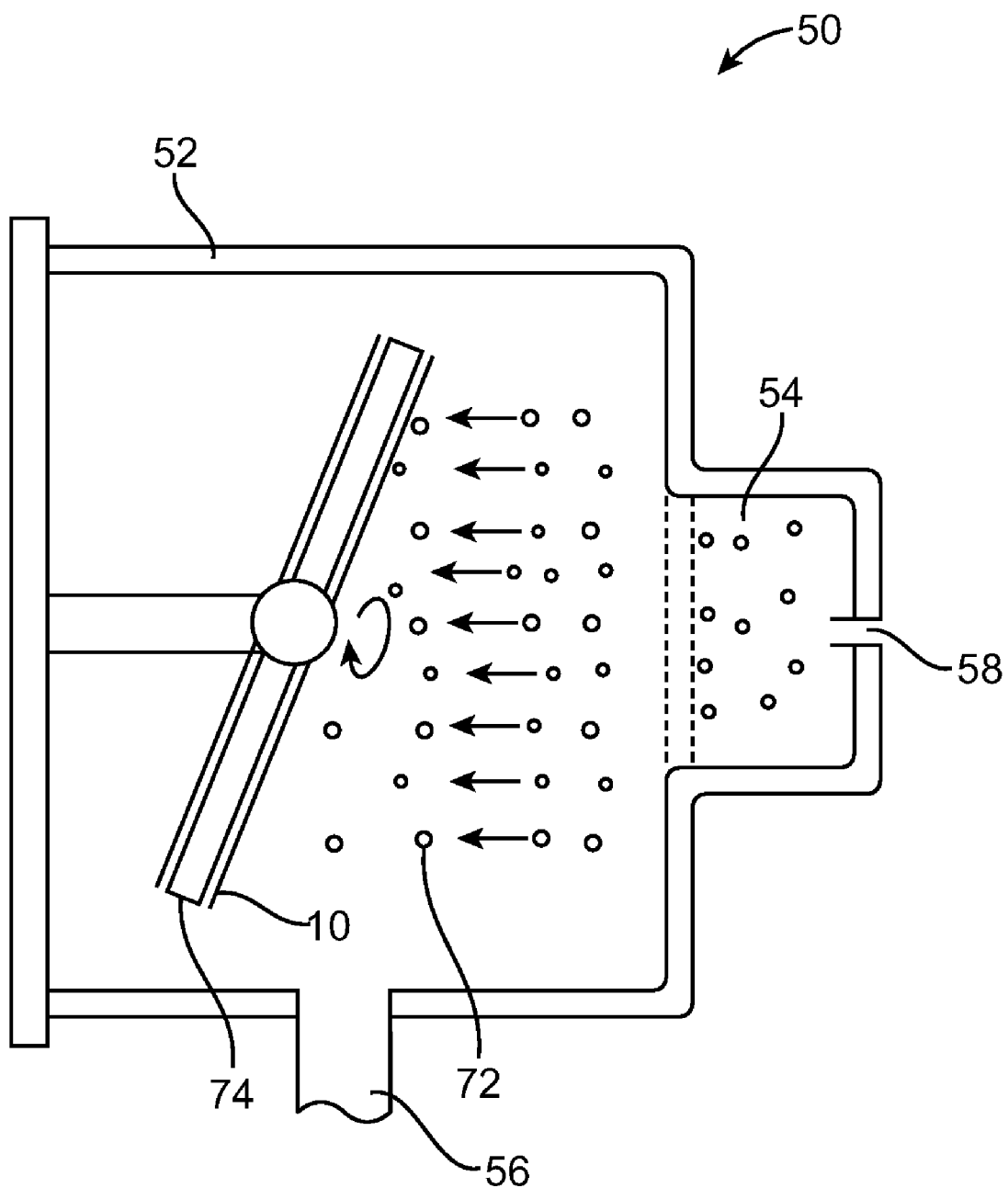
FIG. 8 is a schematic representation of a vapor deposition apparatus that can be used to apply a vaporized drug coating on the surface of an implantable medical device.

Referring now to FIGS. 7-8, a method of coating a stent device is described according to one embodiment of the present invention. FIG. 7 is a flow chart of the method steps, while FIG. 8 is a schematic representation of an example of a vapor deposition apparatus 50. In step 32, the stent undergoes any required surface treatments. For example, a precursor base coating of silane may be applied directly to the stent in a dipping, rolling, spraying, or brushing process. Alternatively, one or more stent surfaces may be roughened as an alternative to the precursor base coating. In step 34, the stent is loaded into a deposition chamber 52 of the vapor deposition apparatus 50.

While loaded in deposition chamber 52 of the vapor deposition apparatus 50, a primer coating may be applied to the stent by vapor phase polymerization in step 36. The primer coating is a polymer coating applied to the stent by vaporizing a dimer, and applying energy to the vaporized dimer such that the polymer is deposited onto the stent. After the primer coating is applied, a quality check may be performed to ensure that it has been properly applied to the stent without removing stent 10 from deposition chamber 52.

Upon suitable application of the primer layer, a drug coating is applied to stent 10 in step 38. More particularly, a drug is introduced into a loading chamber 54 of the vapor deposition apparatus 50. Loading chamber 54 may be maintained at room temperature through the deposition process. The drug is injected into deposition chamber 52, and vaporized therein by heating the drug to a particular temperature. At least a portion of the vaporized drug forms a drug coating on the stent. During at least step 38, a vacuum is utilized to lower the pressure within deposition chamber 52, thereby reducing the temperature necessary to vaporize the drug. The drug may thus be vaporized without breaking down and losing its efficacy. Such a lower pressure reduces the temperature required for vaporizing the drug, thus preserving the efficacy of the drug and allowing it to be deposited onto stent 10 in a vapor phase. By applying the drug in a vapor phase, a uniform and consistent coating is formed on stent 10. In addition, drug vapor deposition allows for improved control over the thickness and weight of the coating, and allows for multiple stents to be coated in one batch in a predictable and repeatable manner. Thus, it will be apparent to those of ordinary skill in the art that multiple stents may be loaded within deposition chamber 52 during the deposition process, such that multiple stents may be coated at one time. When multiple stents are simultaneously coated, the stents must be loaded within deposition chamber 52 in such a manner that each stent is traceable throughout the deposition process. After the drug coating is applied, a quality check may be performed to ensure that it has been properly applied to the stent(s) without removing the stent(s) from deposition chamber 52.

Upon suitable application of the drug coating, a top layer or overcoat is applied to the stent in step 40. The overcoat is deposited over the drug coating to provide a controlled release of the drug when stent 10 is positioned in the vascular system of a patient. While loaded in deposition chamber 52 of vapor deposition apparatus 50, the overcoat may be applied to the stent by vapor phase polymerization. The overcoat is a polymer coating applied to the stent by vaporizing a dimer, and applying energy to the vaporized dimer such that the polymer is deposited onto the stent. After the overcoat is applied, stent 10 may be removed from deposition chamber 52.

It should be understood by those of ordinary skill in the art that the primer coating and the overcoat are not required to be applied by vapor phase deposition as described above in relation to FIG. 7. Rather, the primer coating and the overcoat may be applied in any suitable manner known in the art. However, if applied by vapor phase deposition, steps 36, 38, and 40 as described above may advantageously be performed without removing the stent from the deposition chamber of the vapor deposition apparatus.

Referring to FIG. 8 only, vapor deposition apparatus 50 includes a deposition chamber 52 and a loading chamber 54. A therapeutic substance or drug 72 is introduced into loading chamber 54 through a port 58 at a predetermined flow rate. During the deposition process, loading chamber 54 may be maintained at room temperature. Drug 72 is led into deposition chamber 52, is heated therein such that it changes to a vaporous state, and is deposited onto stent 10 which is placed on a rotatable mandrel 74. Deposition chamber 52 is evacuated by a vacuum pump through an exhaust pipe 56 so that the pressure inside deposition chamber 52 may be in the range of $10^{-3}$ to $10^{-7}$ atm. In an alternative embodiment, stent 10 may be placed into deposition chamber 52 as a flat sheet, in which case mandrel 74 would be replaced by a flat substrate holder.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of coating an implantable medical device comprising the steps of:
   providing an implantable medical device;
   inserting the implantable medical device into a deposition chamber of a vapor deposition apparatus;
   introducing a drug into the deposition chamber;
   lowering the pressure within the deposition chamber containing the drug;
   vaporizing the drug in the deposition chamber at a reduced temperature in response to the lowering of the pressure, and
   depositing the vaporized drug on the implantable medical device to form a drug coating.

2. The method of claim 1, wherein the pressure within the deposition chamber is lowered to approximately $10^{-5}$ atm.

3. The method of claim 1, wherein the drug coating covers at least an outer surface of the implantable medical device.

4. The method of claim 1, wherein the drug coating covers an outer surface and an inner surface of the implantable medical device.

5. The method of claim 1, further comprising the step of:
   applying a precursor base coating layer of silane over a portion of the implantable medical device prior to providing the implantable medical device in the deposition chamber.

6. The method of claim 1, further comprising the step of:
   roughening a portion of the implantable medical device prior to providing the implantable medical device in the deposition chamber.

7. The method of claim 1, further comprising the step of:
applying a primer coating layer over a portion of the implantable medical device after providing the implantable medical device in the deposition chamber but prior to introducing a drug into the deposition chamber.

8. The method of claim 1, further comprising the step of:
applying a top layer of coating material to cover the drug coating, wherein the top layer controls release of the drug when the implantable medical device is placed in situ.

9. The method of claim 8, wherein the top layer of coating material is applied while the implantable medical device is positioned within the deposition chamber.

10. A method of coating a stent comprising the steps of:
providing a stent;
inserting the stent into a deposition chamber of a vapor deposition apparatus;
introducing a drug into the deposition chamber of the vapor deposition apparatus;
lowering the pressure within the deposition chamber containing the drug;
vaporizing the drug in the deposition chamber at a reduced temperature in response to the lowering of the pressure; and
depositing the vaporized drug on the stent to form a drug coating.

11. The method of claim 10, wherein the pressure within the deposition chamber is lowered to approximately $10^{-5}$ atm.

12. The method of claim 10, wherein the drug coating covers at least an outer surface of the stent.

13. The method of claim 10, wherein the drug coating covers an outer surface and an inner surface of the stent.

14. The method of claim 10, further comprising the step of:
applying a precursor base coating layer of silane over a portion of the stent prior to inserting the stent into the deposition chamber.

15. The method of claim 10, further comprising the step of:
roughening a portion of the stent prior to inserting the stent into the deposition chamber.

16. The method of claim 10, further comprising the step of:
applying a primer coating layer over a portion of the stent after inserting the stent into the deposition chamber but prior to introducing the drug into the deposition chamber.

17. The method of claim 10, further comprising the step of:
applying a top layer of coating material to cover the drug coating, wherein the top layer controls release of the drug when the stent is placed in situ.

18. The method of claim 17, wherein the top layer of coating material is applied while the stent is positioned within the deposition chamber.

19. The method of claim 1 wherein lowering the pressure within the deposition chamber containing the drug further comprises applying a vacuum.

20. The method of claim 10 wherein lowering the pressure within the deposition chamber containing the drug further comprises applying a vacuum.

* * * * *